United States Patent [19]

Dunn et al.

[11] Patent Number: 5,200,334
[45] Date of Patent: Apr. 6, 1993

[54] SOL-GEL ENCAPSULATED ENZYME

[75] Inventors: Bruce S. Dunn, Los Angeles; Joan S. Valentine, Encino; Jeffrey I. Zink, Sherman Oaks; Lisa Ellerby, Los Angeles; Fumito Nishida, Los Angeles; Clinton Nishida, Los Angeles; Stacey A. Yamanaka, Los Angeles, all of Calif.

[73] Assignee: The Regents of the University of California, Oakland, Calif.

[21] Appl. No.: 744,524

[22] Filed: Aug. 13, 1991

[51] Int. Cl.$^5$ ............... C12N 11/04; C12N 11/14; C12N 11/08; C03C 3/00
[52] U.S. Cl. ............... 435/182; 435/176; 435/177; 435/180; 501/12
[58] Field of Search ............... 435/176, 177, 180, 182, 435/25, 12; 501/12

[56] References Cited

U.S. PATENT DOCUMENTS

| 3,939,834 | 2/1976 | McMahon | 604/403 |
| 4,639,329 | 1/1987 | Makishima | 252/501.1 |
| 4,680,048 | 7/1987 | Motoki et al. | 65/17 |
| 4,806,328 | 2/1989 | Van Lierop et al. | 423/338 |
| 4,849,378 | 7/1989 | Hench et al. | 501/12 |
| 4,880,851 | 11/1989 | Yamamoto | 523/102 |

FOREIGN PATENT DOCUMENTS 0439318 7/1991 European Pat. Off. ............. 435/176

OTHER PUBLICATIONS

Takeuchi, T. "Sol-Gel Manufacture of Glass", in *Chem. Abs*, 108:61200k, 1988.
Sonogels: An Alternative Method In Sol-Gel Processing by L. Esquivias, et al. *Proceedings of the Third-International Conference on Ultrastructure Processing*, John Wiley & Sons, Inc. (1988), pp. 255, et seq.
Fluorescence Study of Aluminosilicate Sols and Gels Doped with Hydroxy Trisulfonated Pyrene by J. C. Pouxviel, et al. *J. Phys. Chem.* 93, (1989) pp. 2134-2139.
The Optical Behavior of Organic and Organometallic Molecules in Sol-Gel Matrices by D. Dunn, et al. *Mat. Res. Sym.* 121, (1989) pp. 331-342.
Rigidochromism As A Probe of Gelation and Densification of Silicon and Mixed Aluminum-Silicon Alkoxides by J. McKiernan, et al. *J. of Phys. Chem.* 93, (1989), pp. 2129-2133.
Photochromism of Spiropyrans in Aluminosilicate Gels by D. Preston, et al. *J. of Phys. Chem.* 94, (1990) pp. 4167-4172.
Doped Sol-Gel Glasses as Chemical Sensors by R. Zusman, et al. *J. of Non-Crystalline Solids*, 122, (1990) pp. 107-109.
Biochemically Active Sol-Gel Glasses: The Trapping of Enzymes by S. Braun, et al. *Materials Letters*, 10, (Sep. 1990), pp. 1-5.
Building Complex Multimolecule Assemblies Poses Big Challenges by R. Degani *C&EN*, (May 27, 1991), pp. 24-30.
Sol-Gel Science by C. J. Brinker, et al. *Academic Press* (1990), pp. 108-216.

*Primary Examiner*—Ronald W. Griffin
*Assistant Examiner*—Ralph Gitomer
*Attorney, Agent, or Firm*—Sheldon & Mak

[57] ABSTRACT

An active biological material encapsulated in a glass is formed using a sol-gel process. A metal alkoxide is mixed with water and exposed to ultrasonic energy at a pH$\leq$2 to form a single phase solution which is then buffered to a pH between about 5 and 7. The buffered solution is then mixed with the active biological material and the resultant gel is aged and dried. The dried product is a transparent porous glass with substantially all of the added active biological material encapsulated therein, the biological material retaining a high level of activity.

40 Claims, 2 Drawing Sheets

PORE SIZE DISTRIBUTION
MYOGLOBIN IN XEROGEL

SOL-GEL ENCAPSULATED ENZYME

This invention was made with Government support under Grant No. DMR 90-03080 from the National Science Foundation and Grant No. GM 28222 from the National Institutes of Health. The Government may have certain rights in this invention.

BACKGROUND

The present invention relates to a porous glass structure prepared by the sol-gel process. In particular, the invention relates to a porous glass structure which has an active biological material entrapped therein.

Enzymes are commonly used as reactants in manufacturing, catalytic and analytic processes. Encapsulated or entrapped enzymes are used with increasing frequency as micro-catalysts and analytic devices of very high sensitivity. For example, enzymes have been enclosed in membrane systems and used as high-sensitivity monitoring devices.

Such membrane systems, however, are cumbersome and difficult to miniaturize. The enzymatic reactions must be monitored by complex electronic means. Results from the systems are frequently unreliable and nonreproducible.

It would be highly advantageous to encapsulate enzymes in a porous, transparent glass structure, such as, such structures prepared by the sol-gel process. Such an encapsulation would be significantly easier to miniaturize and would be far less cumbersome and far more reliable than membrane encapsulation systems. Furthermore, enzyme encapsulation within a transparent glass structure would allow for the monitoring of many enzymatic reactions by using simple, photometric monitoring systems.

Unfortunately, a high activity enzyme encapsulation system using a porous, transparent glass structure has not as yet been demonstrated. Braun, et al., described in "Biochemically Active Sol-Gel Glasses: The Trapping Of Enzymes," *Materials Letters*, Vol. 10, No. 1, Sept. 2, 1990, pp. 1–5, the encapsulation of an enzyme in a sol-gel glass. The reported activities of the enzyme encapsulated by Braun, et al., was only about 30%, it was not reported whether or not the glass was transparent and the Braun procedure did not result in a monolith.

Accordingly, there is a need for a porous, transparent glass structure which encapsulates an enzyme in such a way that the natural activity of the enzyme is not impaired.

SUMMARY

These needs are met by the present invention. The invention is a protein encapsulated in a porous, transparent glass prepared by the sol-gel process utilizing a unique combination of operating conditions. The process comprises initiating the acid catalyzed hydrolysis of a metal alkoxide in water without added alcohol by applying ultrasonic energy to the metal alkoxide/water combination, buffering the solution to a pH of about 5–6, adding and dispersing the enzyme in the solution, gelling the composition, aging and drying the mixture.

Further, the invention is an optically transparent glass with an extensive, microscopic, interconnecting pore structure having virtually all of a biological material added in the preparation stage entrapped in the structure, with a high percentage of the activity of the biological material being retained.

Still further, the invention is the process for forming the sol-gel glass with entrapped active biological material, particularly thin films as small as 1000 Angstroms thick or shaped gels having dimensions in its smallest direction of at least 0.5 centimeters (a monolith).

The process results in a product useful for forming into sensors for qualitatively and quantitatively detecting the presence of numerous compounds, both organic and inorganic, which react with the entrapped material. Additionally, because of the optical transparency of the glass, photometric detection techniques can be utilized to monitor the changes in the entrapped enzyme or its environment resulting from its use.

DRAWINGS

These and other features, aspects, and advantages of the present invention will become better understood with reference to the following description, appended claims, and accompanying drawings, where:

DESCRIPTION

Figure 1:
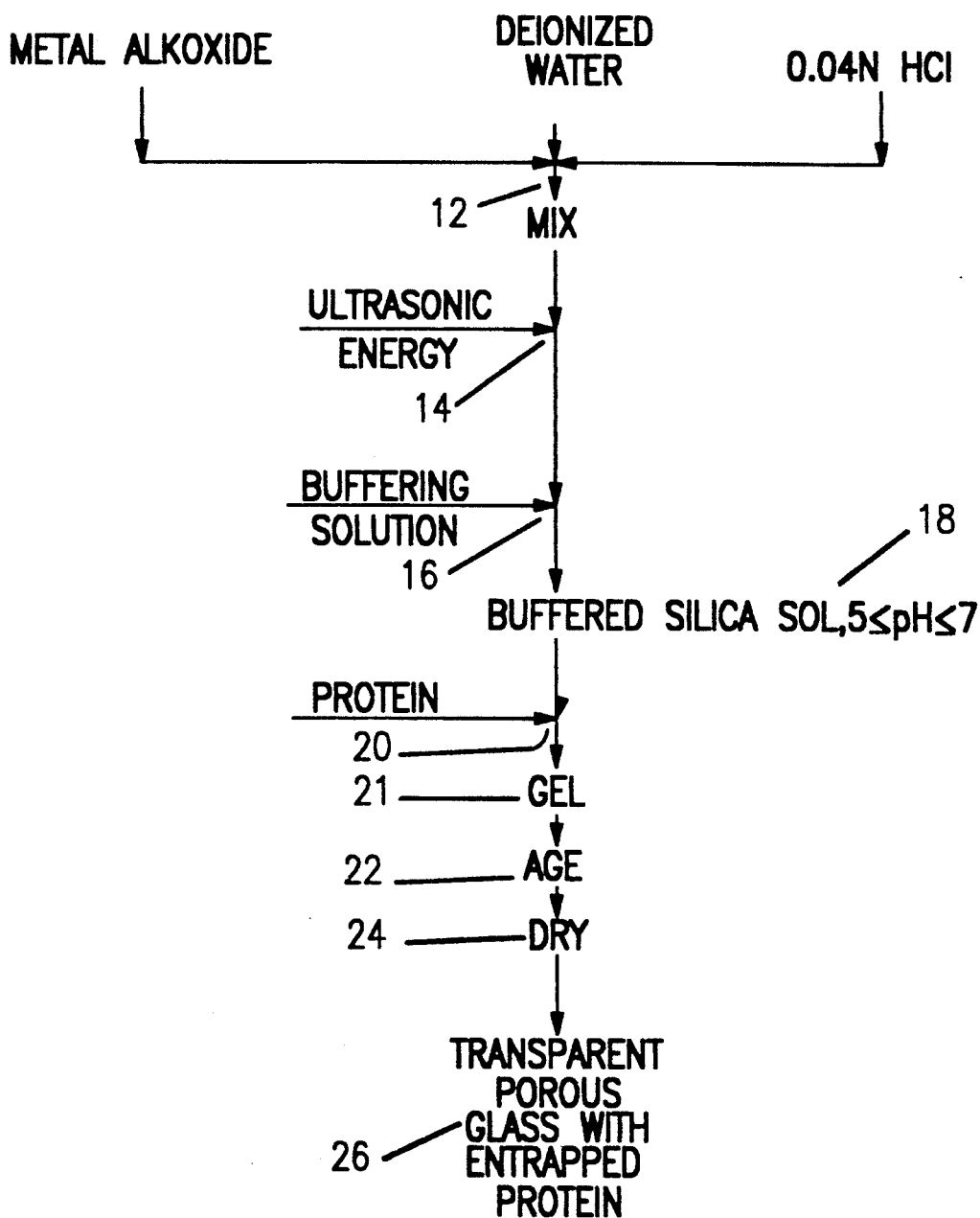
FIG. 1 is a flow diagram depicting an exemplary enzyme encapsulation process having features of the invention.

FIG. 1 depicts an exemplary process embodying features of the invention. A metal alkoxide is mixed with water and an acid catalyst at station 12 to form a solution with a pH of about 2 or less and the mixture is exposed to ultrasonic energy, for example, by placement in an ultrasonic bath at station 14 to assure a uniform mixture and to initiate the polymerization process. The mixture should be removed from the ultrasonic bath before gelation occurs, usually about one to about sixty minutes, preferably about fifteen minutes. After removal of the ultrasonic energy, the mixture, a silica sol, is aged for a short period of time, usually about one to about sixty minutes, preferably about twenty minutes, mixed with a buffer solution at station 16 to raise the pH above about 5, but below 7, preferably between 5 and 6, creating a buffered silica sol 18, and the desired active biological material, such protein is added to the silica sol at station 20. The extent of the aging time is not critical as long as the buffer solution is added before gelation occurs. The mixture is then placed in a plastic container and the container opening is sealed with paraffin, such as a paraffin film sold under the tradename Parafilm ®, to maintain the water content constant. Gelation occurs in about five minutes at a pH of 6, and somewhat slower at pH 5 (about ten to fifteen minutes). The gel 21 is allowed to age in the sealed container for two to 20 or more days, the preferred period being ten to twenty days at station 22 and then dried slowly for several days (for example, 8 days to 4 weeks) at ambient conditions by piercing or removing the paraffin seal at station 24. The result is a transparent glass with entrapped protein 26.

The sol-gel process of the present invention is suitable for the preparation of many different types of oxide glasses and for the entrapment of various different active biological materials. Although, for illustrative purposes, the method is described in respect to a particular precursor compound, namely tetramethylorthosilicate (TMOS), and a particular type of active biological material, namely proteins, it is to be understood that the method is not so limited but is also applicable to other silicon alkoxides such as tetraethylorthosilicate (TEOS) and other active silicon compounds. Besides use of other alkoxides of silicon, the invention contemplates the use of other metal alkoxides prepared by adding methanol, ethanol, isopropanol and other similar alcohols to the oxides of various metals and non-metals, including, but not limited to aluminum, titanium, zirconium, niobium, hafnium, chromium, vanadium, tungsten, molybdenum, iron, tin, phosphorus, sodium, calcium, and boron, or combinations thereof. Additionally, the precursor material or the sol-gel may be tagged by known methods with readily detected substituents, such as optically active groups or constituents which respond to the byproducts of the action of the proteins. Alternatively, other optically active materials may be encapsulated with the protein as indicators of the results of reactions involving the proteins. Other optically active materials include luminescent amino acids, such as tryptophan or other similar materials. Silicon compounds are preferred because silicon chemistry is highly conducive to forming glasses. Among silicon compounds, TMOS is preferred over other materials, such as TEOS, because it reacts faster and does not require alcohol to form a sol.

Further, hydrochloric acid is utilized in the examples but other acids may be utilized to catalyze the reaction between TMOS and water. While HCl is preferred, other suitable acid catalysts include other mineral acids such as sulfuric acid, nitric acid, phosphoric acid, etc. and organic acids such as acetic acid, tartaric acid, phthalic acid, maleic acid, succinic acid and the like and anhydrides of the mineral or organic acids. While acid catalysis is preferred, it is possible to use a base catalyst. However, base catalysts generate rapid gelation, thus making control of the process and the production of monoliths (shaped gels with the smallest dimension greater than a few millimeters) extremely difficult.

Suitable biological materials for encapsulation include, but are not limited to, nucleases, such as RNase A or RNase T1, proteases, such as proteinase K or chymotrypsin, oxidases, such as alcohol oxidase or glucose oxidase, esterases, such as acetylcholine esterase or phosphodiesterase II, isomerases, such as aldolase or glucose isomerase, various proteins including $O_2$ binders, such as hemoglobin or myoglobin, electron transfer proteins, such as cytochrome c, metal and metal ion binders, such as aequorin, iron and bicarbonate binders, such as transferrin, free radical inhibitors, such as superoxide dismutase and other active biologicals such as ureases. One skilled in the art can readily supplement this list with other biological materials which can be entrapped by the process of the invention; the entrapped material not being a limiting factor. Additionally, the biological materials may be modified or tagged by addition of readily detected substituents such as ions, ligands, optically active groups or other constituents commonly used to tag biological or chemical compounds, suitable luminescent tag include $Mn^{2+}$ or other rare earth metal ions.

Figure 2:
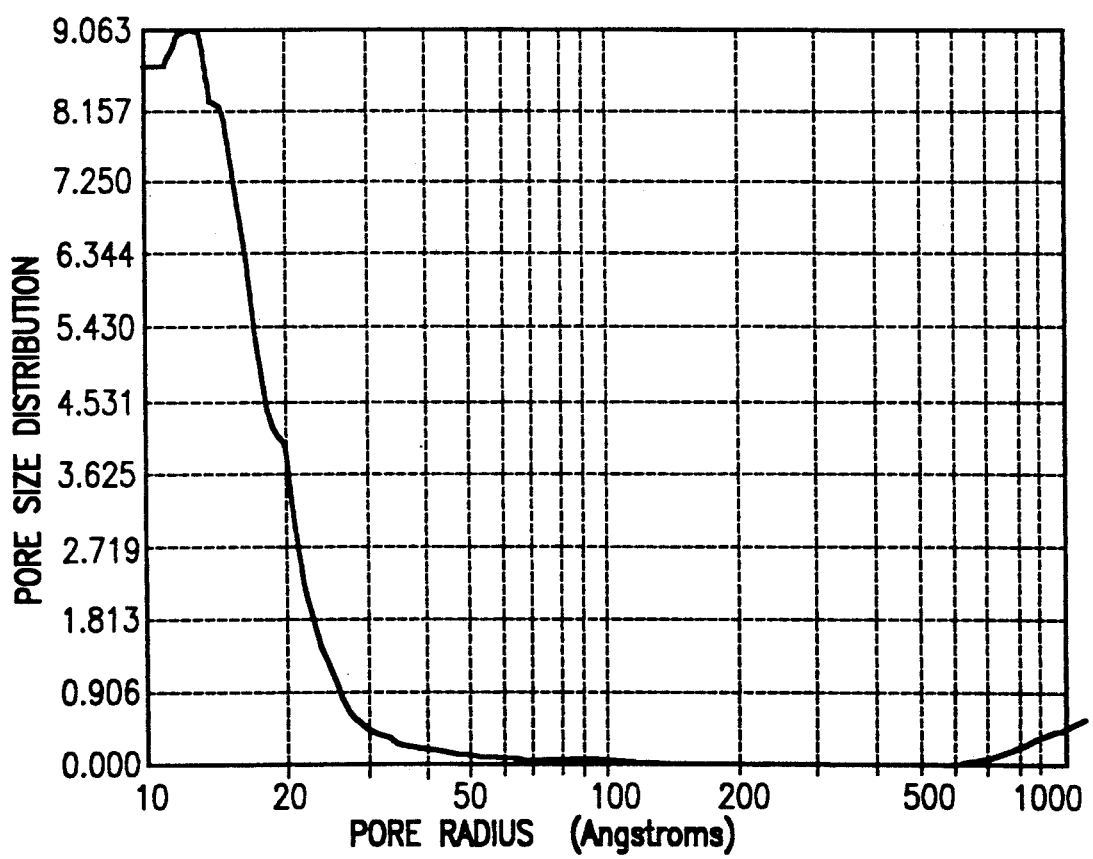
FIG. 2 is a graph showing the pore size distribution in a sol-gel glass made according to the process depicted in FIG. 1.

The resultant product 26 is a porous, transparent glass (a xerogel) with virtually all of the biological material entrapped inside its pores. Because of the preparation conditions selected and the absence of added alcohol, which can destroy or severely reduce the activity of the biological material, the biological material retains a significant portion of its activity, usually in excess of 80%. During the drying process, the mixture shrinks in size resulting in a volume decrease to about 10% to about 15% of its wet state volume. Based on the initial quantity of solids in the mixture, the calculated pore volume of the dried product is from about 20% to about 80%. The properties of the resultant glasses indicate that the process of the invention results in a highly porous structure which, at the same time, has an extensive network of very small diameter interconnecting channels. If the channels were not small, at least a portion of the entrapped biological material would elute from the matrix. If an extensive interconnected structure did not exist the substrate would not be able to reach the active material, thus exhibiting what would appear to be a decrease in the activity of the active material. Additionally, the dimensions of the channels in the porous network must be relatively small, at most no more than about 0.4 microns, or the optical transparency of the glass would be compromised. FIG. 2 is a pore size distribution curve of a typical sol-gel glass with encapsulated protein (myoglobin). Another significant property of the resultant glasses with entrapped biologicals is the storage life of the product. When compared to the storage life of active biological materials not encapsulated, the sol-gel glass entrapped materials have a significantly extended shelf life. Entrapped materials remain active, without significant reduction of activity, for at least seven months as demonstrated by superoxide dismutase entrapped in a sol-gel made according to the process herein described. Other examples include a shelf life in excess of three months for myoglobin and hemoglobin.

As a result of the extremely small pore dimensions, the glasses produced by the process described hereinabove are optically transparent. This property is highly significant when the active biological material is an enzyme and the partially or fully dried sol-gel glass with entrapped enzyme is used as a sensor. The optical clarity of the glass allows optical analytical means to be used to characterize and monitor changes in the enzyme or substrate when exposed to the enzyme. These changes can be directly monitored or fiber optics can be utilized to observe the changes and to transmit optical information to a remote spectroscopic instrument for analysis. For example, enzymes were found to have no change in their spectroscopic properties when entrapped by the described process and the spectroscopic characteristic of the reaction of the enzyme with a substrate were the same as elicited by unbound enzymes. Because of the light transmission characteristics of the glasses, UV, IR and visible light optical spectroscopy as well as fluorescence, luminescence, absorption, emission and reflection techniques are all suitable for quantitative and/or qualitative monitoring of chemical changes produced by the sol-gel glasses with entrapped enzymes prepared according to the invention and sensors utilizing the sol-gel glass entrapped enzymes.

The invention will be further described in connection with the following examples which are set forth for purposes of illustration only.

EXAMPLE 1

Cytochrome c, Myoglobin, Hemoglobin or Superoxide Dismutase 15.22 g of tetramethoxysilane (TMOS), 3.38 g of deionized water, and 0.22 g of 0.04N HCl were added to a plastic beaker, placed in an ultrasonic bath (BRANSON Model 2200 having a well with a 3¼ inch diameter and a 3¼ inch depth or a BRAN- SON Model 3 with a well measuring 5½×9½×4 inch well) and stirred for about 15 minutes. The resultant single phase sol was aged at room temperature for twenty minutes and a buffered sol was then prepared by mixing equal amounts of buffer solution and silica sol, i.e., 2 mL of 0.01M sodium phosphate or 2 mL of 0.001M sodium acetate with 2 mL of the silica sol. The desired amount of active biological material (cytochrome c, myoglobin, hemoglobin or superoxide dismutase) was then added to, and dispersed in the buffered sol in the quantities listed in Table 1. For example, Sample 5, Table 1 specifies 4.0 ml sol, 4.0 ml buffer and 2.0 ml of 0.01 mM cytochrome c. The biological containing buffered sol was poured into a 4 mL polystyrene cuvette and the opening in the cuvette was sealed using a paraffin film. The material was allowed to age in the sealed container for 7 to 21 days. The paraffin film was then pierced and the mixture was allowed to dry for 10 to 60 days. The resultant product was a transparent colored porous glass with the biological material entrapped therein. The sol-gel glass superoxide dismutase was blue-green in color, the sol-gel glass containing cytochrome c was colored deep red, and the sol-gel glass myoglobin was colored beige or pale orange. A typical mixture contained about 0.10 g of solid material (TMOS, phosphate from the buffer and active biological material) and about 0.9 g of evaporatable liquid (10 to 15% solids). Upon drying, the mixture shrinks to about 12.5% of its original volume resulting in about 50% voids and an apparent density of 1.2g/cc.

It has also been found that the entrapped active biological material has an improved shelf life over that of the comparable free biological material stored at room temperature. An encapsulated superoxide dismutase has been demonstrated to have a shelf life in excess of 210 days without any significant decrease in activity or spectroscopic changes. In contrast thereto, the same material stored at room temperature in solution will show a much greater loss of activity for the same time period.

TABLE 1

Summary of Sol Gel Samples

| | Protein | [Protein] | Volume Protein | Volume Buffer | Volume Sol | Buffer | Temperature |
|---|---|---|---|---|---|---|---|
| 1 | Glucose Oxidase (GO) | .0048 mM | .40 mL | .80 mL | .80 mL | .001 M NaAc pH 6.0 | RT |
| 2 | Superoxide Dismutase | .5 mM | 2.0 mL | 4.0 mL | 4.0 mL | .001 M NaAc pH 6.0 | RT |
| 3 | Superoxide Dismutase | .5 mM | 2.0 mL | 4.0 mL | 4.0 mL | .001 M NaAc pH 6.0 | RT |
| 4 | Superoxide Dismutase | .125 mM | 6.0 mL | 12.0 mL | 12.0 mL | .001 M NaAc pH 6.0 | RT |
| 5 | Cytochrome c | .01 mM | 2.0 mL | 4.0 mL | 4.0 mL | .001 M NaAc pH 6.0 | RT |
| 6 | Cytochrome c | .10 mM | 2.0 mL | 4.0 mL | 4.0 mL | .001 M NaAc pH 6.0 | RT |
| 7 | Cytochrome c | .0025 mM | 6.0 mL | 12.0 mL | 12.0 mL | .001 M NaAc pH 6.0 | RT |
| 8 | Cytochrome c | .01 mM | 6.0 mL | 12.0 mL | 12.0 mL | .001 M NaAc pH 6.0 | RT |
| 9 | Myoglobin | .002 mM | 6.0 mL | 12.0 mL | 12.0 mL | .001 M NaAc pH 6.0 | RT |
| 10 | Myoglobin | .008 mM | 2.0 mL | 4.0 mL | 4.0 mL | .001 M NaAc pH 6.0 | RT |
| 11 | Myoglobin | 1.0 mM | 1.0 mL | 2.0 mL | 2.0 mL | .001 M NaAc pH 6.0 | RT |
| 12 | Myoglobin | 0.25 mM | 1.0 mL | 2.0 mL | 2.0 mL | .001 M NaAc pH 6.0 | RT |
| 13 | Myoglobin | 1.0 mM | .40 mL | .80 mL | .80 mL | .001 M NaAc pH 6.0 | RT |
| 14 | Glucose Oxidase | .05 mM | 1.0 mL | 2.0 mL | 2.0 mL | .001 M NaAc pH 6.0 | RT |
| 15 | Glucose Oxidase | .0125 mM | .40 mL | .80 mL | .80 mL | .001 M NaAc pH 6.0 | RT |
| 16 | Glucose Oxidase | .005 mM | 1.0 mL | 2.0 mL | 2.0 mL | .001 M NaAc pH 6.0 | RT |
| 17 | Glucose Oxidase | .005 mM | .40 mL | .80 mL | .80 mL | .001 M NaAc pH 6.0 | RT |
| 18 | Glucose Oxidase | .0001 mM | 1.0 mL | 2.0 mL | 2.0 mL | .001 M NaAc pH 6.0 | RT |
| 19 | Glucose Oxidase | .01 mM | 1.0 mL | 2.0 mL | 2.0 mL | .001 M NaAc pH 6.0 | RT |
| 20 | Glucose Oxidase | .001 mM | 1.0 mL | 2.0 mL | 2.0 mL | .001 M NaAc pH 6.0 | RT |
| 21 | Peroxidase (PO) | 1.3 mg/ml | 1.0 mL | 2.0 mL | 2.0 mL | .01 M Phos. pH 6.0 | RT |
| 22 | Peroxidase | 1.3 mg/ml | .50 mL | 1.25 mL | .75 mL | .01 M Phos. pH 6.0 | 4 C |
| 23 | Glucose Oxidase | .05 mM | .50 mL | 1.25 mL | .75 mL | .01 M Phos. pH 6.0 | 4 C |
| 24 | Trinder | bot/10 mL | Bot/10 mL | 0 | 2.0 mL | Trinder pH 7.0 | RT |
| 25 | Hemoglobin | 1 mM | 1.0 mL | 2.0 mL | 2.0 mL | .01 M Phos. pH 6.0 | RT |
| 26 | Hemoglobin | .01 mM | 1.0 mL | 2.0 mL | 2.0 mL | .01 M Phos. pH 6.0 | RT |
| 27 | Hemoglobin | .05 mM | 1.0 mL | 2.0 mL | 2.0 mL | .01 M Phos. pH 6.0 | RT |
| 28 | PO & GO | .39, .05 units | 1.0 mL | 2.0 mL | 2.0 mL | .01 M Phos. pH 6.0 | 4 C |
| 29 | PO & GO | 1.95, .3 units | 1.0 mL | 2.0 mL | 2.0 mL | .01 M Phos. pH 6.0 | 4 C |
| 30 | PO & GO | 3.9, .56 units | 1.0 mL | 2.0 mL | 2.0 mL | .01 M Phos. pH 6.0 | 4 C |
| 31 | PO & GO | 7.8, 1.1 units | 1.0 mL | 2.0 mL | 2.0 mL | .01 M Phos. pH 6.0 | 4 C |
| 32 | PO & GO | 15.6, 2.2 units | 1.0 mL | 2.0 mL | 2.0 mL | .01 M Phos. pH 6.0 | 4 C |
| 33 | Trinder | bot/50 mL | 9.0 mL | 0 | 6.0 mL | Trinder pH 6.0 | 4 C |
| 34 | Trinder | bot/50 mL | 18.0 mL | 0 | 12.0 mL | Trinder pH 6.0 | 4 C |
| 35 | Trinder | bot/50 mL | 5.0 mL | 0 | 3.33 mL | Trinder pH 5.0 | 4 C |
| 36 | Glucose Oxidase* | 2.8 units | 4.0 mL | 9.0 mL | 7.0 mL | .01 M Phos. pH 6.0 | 4 C |
| 37 | Glucose Oxidase* | 1.1 units | 4.0 mL | 9.0 mL | 7.0 mL | .01 M Phos. pH 6.0 | 4 C |
| 38 | Glucose Oxidase* | .55 units | 4.0 mL | 9.0 mL | 7.0 mL | .01 M Phos. pH 6.0 | 4 C |
| 39 | Glucose Oxidase* | .28 units | 4.0 mL | 9.0 mL | 7.0 mL | .01 M Phos. pH 6.0 | 4 C |
| 40 | Glucose Oxidase* | .055 units | 4.0 mL | 9.0 mL | 7.0 mL | .01 M Phos. pH 6.0 | 4 C |
| 41 | Peroxidase* | 5.75 units | 4.0 mL | 9.0 mL | 7.0 mL | .01 M Phos. pH 6.0 | 4 C |
| 42 | Peroxidase* | .92 units | 4.0 mL | 9.0 mL | 7.0 mL | .01 M Phos. pH 6.0 | 4 C |
| 43 | Peroxidase* | .46 units | 4.0 mL | 9.0 mL | 7.0 mL | .01 M Phos. pH 6.0 | 4 C |
| 44 | Peroxidase* | .23 units | 4.0 mL | 9.0 mL | 7.0 mL | .01 M Phos. pH 6.0 | 4 C |
| 45 | Peroxidase* | .046 units | 4.0 mL | 9.0 mL | 7.0 mL | .01 M Phos. pH 6.0 | 4 C |
| 46 | PO & GO* | .12, .02 units | 4.0 mL | 9.0 mL | 7.0 mL | .01 M Phos. pH 6.0 | 4 C |
| 47 | PO & GO* | .35, .07 units | 4.0 mL | 9.0 mL | 7.0 mL | .01 M Phos. pH 6.0 | 4 C |
| 48 | PO & GO* | 1.2, .2 units | 4.0 mL | 9.0 mL | 7.0 mL | .01 M Phos. pH 6.0 | 4 C |
| 49 | PO & GO* | 3.4, 1.2 units | 4.0 mL | 9.0 mL | 7.0 mL | .01 M Phos. pH 6.0 | 4 C |
| 50 | Trinder | bot/50 mL | 26.0 mL | 0 | 13.5 mL | Trinder pH 6.0 | 4 C |
| 51 | Glucose Oxidase | 2.8 units | 2.0 mL | 3.3 mL | 2.7 mL | .01 M Phos. pH 6.0 | 4 C |
| 52 | Glucose Oxidase | 1.1 units | 2.0 mL | 3.3 mL | 2.7 mL | .01 M Phos. pH 6.0 | 4 C |

TABLE 1-continued

Summary of Sol Gel Samples

| Protein | [Protein] | Volume Protein | Volume Buffer | Volume Sol | Buffer | Temperature |
|---|---|---|---|---|---|---|
| 53 Glucose Oxidase | .55 units | 2.0 mL | 3.3 mL | 2.7 mL | .01 M Phos. pH 6.0 | 4 C |
| 54 Peroxidase | 5.75 units | 2.0 mL | 3.3 mL | 2.7 mL | .01 M Phos. pH 6.0 | 4 C |
| 55 Peroxidase | .9 units | 2.0 mL | 3.3 mL | 2.7 mL | .01 M Phos. pH 6.0 | 4 C |
| 56 Peroxidase | .5 units | 2.0 mL | 3.3 mL | 2.7 mL | .01 M Phos. pH 6.0 | 4 C |
| 57 PO & GO | 3.5, 1.1 units | 2.0 mL | 3.3 mL | 2.7 mL | .01 M Phos. pH 6.0 | 4 C |
| 58 PO & GO | 1.1, .2 units | 2.0 mL | 3.3 mL | 2.7 mL | .01 M Phos. pH 6.0 | 4 C |
| 59 PO & GO | .35, .07 units | 2.0 mL | 3.3 mL | 2.7 mL | .01 M Phos. pH 6.0 | 4 C |
| 60 Superoxide Dismutase | .5 mM | 1.0 mL | 2.0 mL | 2.0 mL | .01 M Phos. pH 6.0 | RT |

*Sol prepared with more acid and less TMOS
30.44 gm TMOS
7.2 g 0.04 M HCl
7.2 g ddH2O FIG. 2 is a graph showing the pore size and distribution of pore sizes in the dried sol-gel glass (xerogel) encapsulating myoglobin determined using gas adsorption techniques, the y axis being dimensionless numbers, experimentally derived, which show the relative concentration of pores of different sizes. The mean of the radii is about 15 Angstroms, a high percentage (80% or more) of the pores have radii below 30 Angstrom in size and the maximum pore radii is about 100 Angstroms. The apparent density of the glass is 1.2g/cc and the specific surface area, derived mathematically from FIG. 2, is between 400 and 800m$^2$/g. Xerogels containing other active biological materials prepared as described above showed similar properties. This combination of properties is believed to be unique and to be a result of the processing conditions described above.

EXAMPLE 2

Peroxidase or Glucose Oxidase

A single phase sol was prepared in an ultrasonic bath using (a) the quantities listed in Example 1, or (b) 30.44g TMOS, 7.2g 0.04M HCl and 7.2 g double deionized water and aged following the procedure of Example 1. In accordance with Table 1, a quantity of the single phase sol was then cooled to 10° C., mixed with a buffering solution of sodium phosphate cooled to about the same temperature, the mixture was aged for 2 min in an ice bath, and an amount of buffered peroxidase or glucose oxidase solution in quantities and concentrations listed in Table 1 and cooled to 2° C. was added to the cold buffered sol. The cold mixture was aged for 7 to 20 days in a refrigerator at about 4° C., the paraffin film was punctured and the sol was allowed to dry for 10 to 60 days while being held either 4° C. or room temperature. The resultant product, was a catalytically active, transparent porous glass having the peroxidase or glucose oxidase entrapped in the porous structure.

EXAMPLE 3

Trinder ® (Glucose) Reagent

A single phase sol was prepared and aged following the procedure of FIG. 1 and then cooled to less than 10° C. Trinder (glucose) reagent was reconstituted in doubly deionized water (50 mL). The reconstituted solution contained 4-aminoantipyrine (1.0 mmol/L), p-hydroxybenzene sulfonate (40 mmol/L), peroxidase from horseradish (20,000 units/L) and buffer at pH 7.0. The pH of the Trinder (glucose) reagent was then adjusted to a pH between 5 and 6, using 1.5N phosphoric acid, cooled to 4° C., and the desired amount (see Table 1) was added to the chilled single phase sol at a ratio of three parts reagent to 2 parts silica sol. The cold mixture was placed in a cuvette, sealed with a paraffin film, and aged for 7 to 20 days in a refrigerator at 4° C. The paraffin film was then punctured to allow the mixture to dry while being held for 10 to 60 days at 4° C. The resultant product, a transparent, colored porous glass with the biological material entrapped in the porous structure underwent a color change with an increase in absorption at 500nm when exposed to glucose.

The enzymatic activity of glucose oxidase in combination with peroxidase as well as the activity of the Trinder reagent was tested by exposing the entrapped glucose oxidase to β-D-glucose and o-dianisidine. It is known that glucose oxidase catalyzes the oxidation of β-D-glucose to D-gluconic acid and hydrogen peroxide. The peroxidase then uses hydrogen peroxide to catalyze the oxidation of o-dianisidine resulting in a colorimetric change at 500 nm (red solution). The identical color change (both quantitatively and qualitatively) was observed in aged, dried glucose oxidase-peroxidase gels.

In order to determine if the active biological material was evenly distributed throughout the gel, the sol-gel with entrapped material was sliced into several pieces. All slices showed the same response—an intense red color when exposed to the solutions described above. In order to determine if the active biological material was, in fact, encapsulated into the glass and would not leach out of the porous material, the glucose oxidase-peroxidase gels were repeatedly washed with buffered solution and the activity of the wash solutions were tested by addition of β-D-glucose and o-dianisidine. No color change was observed in any of the wash solutions.

Trinder solutions were tested in a like manner. Gels prepared from a Trinder reagent having a pH=7 showed no color change when exposed to glucose. Additionally, when these gels were washed with buffer the Trinder solution was shown to be leached from the sol-gel glass as evidenced by a red color in the wash solution when exposed to glucose. However, preparation of the sol-gel glass with a Trinder solution buffered to either pH=5 or 6 resulted in glasses which showed the red color response when exposed to glucose and washing solutions were unable to leach the active material from the glass as shown by an absence of the red color response in the wash solutions.

To determine the effectiveness of the encapsulation process on other biological materials the following tests were performed:

a. A gel was prepared from 1.0 mM bovine CuZn-SOD (copper zinc superoxide dismutase) in 1 mM NaOAc buffer (pH 5.8). A portion of the aged gel was then dried to form a xerogel. The visible absorption spectra for an aged gel with entrapped material as well as the glass resulting from drying the gel was unchanged from the spectra of the same CuZnSOD in solution and exhibited the characteristic d-d transition (680nm) and the imidazolate-to-Cu charge transfer transition (420nm shoulder). After treatment of the xerogel with 100mM EDTA solution (pH=3.8) the copper absorption band disappeared. This is the same response seen when CuZnSOD in solution is dialyzed against EDTA. The original gel spectra can be restored by treating the gel with several aliquots of 100 mM $CuSO_4$ at pH=5.5 followed by several aliquots of 1M $ZnSO_4$ at pH=5.5. A similar response was seen when a xerogel was exposed to EDTA and then treated with $CuSO_4$ followed by $ZnSO_4$.

b. The visible absorption spectra of cytochrome c in aged gels and xerogels had no detectable difference from the same materials in solution. In addition, the entrapped cytochrome c can be reduced by the addition of sodium dithionite in the same manner as cytochrome c in solution. On exposure to air the encapsulated material spontaneously reoxidized without any deterioration of its spectroscopic properties.

c. Encapsulated myoglobin and hemoglobin prepared in accordance with the procedures set forth above have been compared to the same biological materials in solution. Spectroscopic analysis has shown that the myoglobin and hemoglobin retain their native structure and react with $O_2$ and CO in the same manner as free myoglobin and hemoglobin.

Although the present invention has been described in considerable detail with reference to certain preferred versions and uses thereof, other versions and uses are possible. For example, the time and temperature for various steps in the process can be varied. In particular, the time and temperature in the ultrasonic bath, the aging step prior to buffering the solution, and the aging of the gel after addition of the active biological material can be eliminated, shortened or extended. Additionally, the drying step can be performed more rapidly or slower depending on the temperature and exposed surface area of the gel. However, if drying is performed too rapidly optically useful monoliths can be difficult to produce as the xerogel can develop cracks. The most critical factor limiting the time allotted for aging and drying is the surface area and volume of the gel. Additionally, it is not necessary for the xerogel to be fully dried to be used as sensors or in other applications. Partially dried xerogels prepared by the process described exhibit the same or similar properties as fully dried gels.

The process described has utility for preparing porous, transparent glasses with various different active materials or combinations of materials entrapped therein, the process not being limited to proteins. In addition, while the products have a primary utility as sensors or catalysts, they are useful for preparing unique optical materials for other applications. Glasses prepared as described above have utility as lasers, when suitable dyes, such as rhodamine or coumarins, are incorporated in the xerogel. The process also has utility to prepare photoelectrochemical cells. Therefore, the spirit and scope of the appended claims should not be limited to the description of the preferred versions contained herein.

What is claimed is:

1. A process for the production of a porous, transparent sol-gel glass containing an alcohol sensitive active biological material entrapped therein comprising:
   (a) forming a single phase sol by mixing a metal alkoxide in a non-alcoholic medium comprising water and an acid catalyst in a container exposed to ultrasonic energy, the mixture having a pH not greater than about 2;
   (b) removing the ultrasonic energy and raising the pH of the sol to about 5 to 7 by the addition of a buffering agent;
   (c) adding said active biological material to the buffered sol;
   (d) forming a gel and allowing the gel to age; and
   (e) allowing at least a portion of the water in the gel to evaporate so that the volume of the product produced in step (d) is decreased and the active biological material is trapped in a monolith of the gel having a reduced volume.

2. The process of claim 1 wherein a pre-buffer aging step is added after exposing the mixture to ultrasound but prior to buffering the mixture.

3. The process of claim 1 wherein the gel is aged for at least about ten days.

4. The process of claim 1 wherein step(e) continues for at least about ten days.

5. The process of claim 1 wherein the active biological material is a protein.

6. The process of claim 1 wherein the active biological material is selected from the group consisting of nuclease, protease, oxidase, esterase, isomerase, metal and metal ion binders, bicarbonate binders, free radical inhibitors, reversible oxygen binders and combinations thereof.

7. The process of claim 1 wherein the active biological material is selected from the group consisting of RNase A, RNase T1, protease k, chymotrypsin, alcohol oxidase, glucose oxidase, acetylcholine esterase, phosphodiesterase II, aldolase, glucose isomerase, hemoglobin, myoglobin, cytochrome c, aequorin, transferase, urease, superoxide dismutase and combinations thereof.

8. The process of claim 1 wherein the resultant product is a three dimensional object with a smallest dimension being from about 1000 Angstroms to about 0.5 cm.

9. The process of claim 1 wherein the volume of the product of step (e) is reduced to about twelve percent (12%) of the volume of the product of step (d).

10. The process of claim 1 wherein the gel is aged for about 2 days to about 21 days.

11. The process of claim 1 wherein the aged gel is dried for about 8 days to about 60 days.

12. A porous, transparent sol-gel glass having entrapped therein an active biological material wherein the glass is prepared by:
   (a), forming a single phase sol by mixing a metal alkoxide in a non-alcoholic medium comprising water and an acid catalyst and exposing the mixture to ultrasonic energy, the mixture having a pH not greater than about 2;
   (b) removing the ultrasonic energy and raising the pH of the sol to about 5 to 7 by the addition of a buffering agent;

(c) adding an active biological material to the buffered sol;
(d) forming a gel and allowing the gel to age; and
(e) allowing at least a portion of the water in the gel to evaporate so that external dimensions of the gel produced in step (d) are reduced and the active biological material is held within the structure after evaporation.

13. The porous transparent sol-gel glass of claim 12 wherein a pre-buffer aging step is added after exposing the mixture to ultrasound but prior to buffering the mixture.

14. The porous transparent glass of claim 12 wherein the gel is aged for at least about ten days.

15. The porous transparent glass of claim 14 wherein the aged gel is dried for at least about ten days.

16. The porous transparent glass of claim 12 wherein the active biological material is a protein.

17. The porous transparent glass of claim 12 wherein the active biological material is selected from the group consisting of nuclease, protease, oxidase, esterase, isomerase, metal and metal ion binders, bicarbonate binders, free radical inhibitors, reversible oxygen binders and combinations thereof.

18. The porous transparent glass of claim 12 wherein the active biological material is selected from the group consisting of RNase A, RNase T1, protease k, chymotrypsin, alcohol oxidase, glucose oxidase, acetylcholine esterase, phosphodiesterase II, aldolase, glucose isomerase, hemoglobin, myoglobin, cytochrome c, aequorin, transferase, urease, superoxide dismutase and combinations thereof.

19. The porous transparent sol-gel glass of claim 12 wherein the volume of the structure produced by evaporation is reduced to about twelve percent (12%) of the volume of the gel produced in step (d).

20. The porous transparent glass of claim 12 wherein the gel is aged for about 2 days to about 21 days.

21. The porous glass of claim 12 wherein the aged gel is dried for about 8 days to about 60 days.

22. A porous, transparent sol-gel glass having an apparent density of 1.2 g/cc, a specific surface area of about 400 to 800 m$^2$/g, a median pore radius of about 15 Angstroms and a maximum pore radius of about 100 Angstroms, the porous, transparent glass having an active biological material entrapped therein.

23. The porous, transparent sol-gel glass of claim 22 wherein the active biological material is selected from the group consisting of nuclease, protease, oxidase, esterase, isomerase, metal and metal ion binders, bicarbonate binders, free radical inhibitors, reversible oxygen binders and combinations thereof.

24. The porous transparent sol-gel glass of claim 22 wherein the active biological material is selected from the group consisting of RNase A, RNase T1, protease k, chymotrypsin, alcohol oxidase, glucose oxidase, acetylcholine esterase, phosphodiesterase II, aldolase, glucose isomerase, hemoglobin, myoglobin, cytochrome c, aequorin, transferase, urease, superoxide dismutase and combinations thereof.

25. A method for the qualitative or quantitative detection of a substance which reacts with or whose reaction is catalyzed by an active biological material which comprises:
(1) The production of a porous, transparent sol-gel glass containing an active biological material entrapped therein comprising:

(a) forming a single phase sol by mixing a metal alkoxide in a non-alcoholic medium comprising water and an acid catalyst in a container exposed to ultrasonic energy, the mixture having a pH not greater than about 2;
(b) removing the ultrasonic energy and raising the pH of the sol to about 5 to 7 by the addition of a buffering agent;
(c) adding an active biological material to the buffered sol;
(d) forming a gel and allowing the gel to age; and
(e) allowing at least a portion of the water in the gel to evaporate causing the gel to shrink and the active biological material to be trapped in the porous glass.

(2) Brining the porous, transparent glass containing the active biological material into contact with an aqueous solution of the substance; and
(3) Observing the change in optical characteristics of the porous, transparent glass containing an active biological material.

26. The method of claim 25 wherein the change in optical characteristics is observed using spectroscopic techniques.

27. The method of claim 26 wherein the spectroscopic techniques are selected from the group consisting of UV, IR, visible light, fluorescence, luminescence, absorption, emission and reflection techniques.

28. The method of claim 25 wherein a pre-buffer aging step is added after exposing the mixture to ultrasound but prior to buffering the mixture.

29. The method of claim 25 wherein the gel is aged for at least about ten days.

30. The method of claim 29 wherein the aged gel is dried for at least about ten days.

31. The method of claim 25 wherein the active biological material is a protein.

32. The method of claim 25 wherein the active biological material is selected from the group consisting of nuclease, protease, oxidase, esterase, isomerase, metal and metal ion binders, bicarbonate binders, free radical inhibitors, reversible oxygen binders and combinations thereof.

33. The method of claim 25 wherein the active biological material is selected from the group consisting of RNase A, RNase T1, chymotrypsin, alcohol oxidase, glucose oxidase, acetylcholine esterase, phosphodiesterase II, aldolase, glucose isomerase, hemoglobin, myoglobin, cytochrome c, aequorin, transferase, urease, superoxide dismutase and combinations thereof.

34. The method of claim 25 wherein the porous transparent sol-gel glass is prepared in the form of a film with a thickness of greater than about 1000 Angstroms.

35. The method of claim 25 wherein the porous transparent sol-gel glass is prepared in the form of a monolith with a smallest dimension less than about 0.5 centimeters.

36. The method of claim 26 wherein the porous transparent sol-gel glass is prepared in the form of a three dimensional structure having a shortest dimension between about 1000 Angstroms and about 0.5 centimeters.

37. The method of claim 25 wherein the porous glass formed in step (1) (e) has a volume of about twelve percent (12%) of the volume of the gel formed in step (1) (d).

38. The method of claim 25 wherein the gel is aged for about 2 days to about 21 days.

39. The method of claim 25 wherein the aged gel is dried for about 8 days to about 60 days.

40. A process for the production of a porous, transparent aged gel containing an alcohol sensitive active biological material entrapped therein comprising:
(a) forming a single phase sol by mixing a metal alkoxide in a non-alcoholic medium comprising water and an acid catalyst in a container exposed to ultrasonic energy, the mixture having a pH not greater than about 2;
(b) removing the ultrasonic energy and raising the pH of the sol to about 5 to 7 by the addition of a buffering agent;
(c) adding an active biological material to the buffered sol; and
(d) forming a gel and allowing the gel to age.

* * * * *